United States Patent [19]

Dunsmuir et al.

[11] Patent Number: 5,633,440
[45] Date of Patent: May 27, 1997

[54] P119 PROMOTERS AND THEIR USES

[75] Inventors: Pamela Dunsmuir, Piedmont; Jamie S. Stott, Oakland, both of Calif.

[73] Assignee: DNA Plant Technology Corporation, Oakland, Calif.

[21] Appl. No.: 359,696

[22] Filed: Dec. 20, 1994

[51] Int. Cl.$^6$ ............................ A01H 5/00; C12N 15/29; C12N 15/82; C12N 5/04
[52] U.S. Cl. ................................ 800/205; 800/DIG. 40; 800/DIG. 43; 800/DIG. 44; 435/172.3; 435/320.1; 536/23.6; 536/24.1
[58] Field of Search .................... 536/23.6, 24.1; 435/172.3, 320.1; 800/205, DIG. 43, DIG. 40, DIG. 44

[56] References Cited

U.S. PATENT DOCUMENTS 4,943,674  7/1990  Houck et al. ........................ 800/205

OTHER PUBLICATIONS

Deikman, Jill, et al. (1988) "Interaction of a DNA binding factor with the 5'-flanking region of an ethylene-responsive fruit ripening gene from tomato", *The EMBO Journal*, 7(11):3315–3320.

Cordes, Sabine, et al. (1989) "Interaction of a Developmentally Regulated DNA–Binding Factor with Sites Flanking Two Different Fruit–Ripening Genes from Tomato", *The Plant Cell*, 1:1025–1034.

DellaPenna, Dean, et al. (1986) "Molecular cloning of tomato fruit polygalacturonase: Analysis of polygalacturonase mRNA levels during ripening", *Proc. Natl. Acad. Sci. USA*, 83:6420–6424.

Iusem, N.D., et al. [(1993) *Plant Physiol.*, 102(4):1353–4], "Corrections", *Plant Physiol.* (1994) 104:307.

Iusem et al. 1993. Plant Physiol. 102(4):1353–4.

Picton et al. 1993. Plant Mol. Biol. 23(1):183–207.

*Primary Examiner*—David T. Fox
*Attorney, Agent, or Firm*—Townsend and Townsend and Crew LLP

[57] ABSTRACT

This invention relates to compositions and methods useful in the production of transgenic plants. In particular, the invention relates to P119 plant promoter sequences and to expression cassettes containing P119 plant promoter sequences. The invention also relates to vectors and transgenic plants containing P119 plant promoter sequences that are operably linked to heterologous DNA sequences. In addition, the invention relates to methods of producing transgenic plants by using vectors containing P119 promoter sequences.

22 Claims, 1 Drawing Sheet

P119 PROMOTERS AND THEIR USES

BACKGROUND OF THE INVENTION

This invention relates to compositions and methods useful in the production of transgenic plants. In particular, the invention relates to plant promoter sequences providing tissue specific expression of desired nucleic acids.

Isolated plant promoters are useful in the genetic engineering of plants to produce transgenic plants with desired phenotypic characteristics. In order to produce such transgenic plants, an isolated plant promoter is inserted into a vector and operably linked to a heterologous DNA sequence. Plant cells can then be transformed in a variety of ways by DNA constructs containing an isolated plant promoter fused to heterologous DNA sequences. The result of this transformation is that the plant promoter operably linked to the heterologous DNA is inserted into the genome of the transformed plant cell. Furthermore, the regulation of the heterologous DNA in the transformed plant cell can be controlled by the expression of the promoter.

There are a variety of different approaches for producing a desired phenotype in a transgenic plant, depending on the nature of the heterologous sequences coupled to the isolated plant promoter. For example, expression of a novel gene that is not normally expressed in plant or in a particular tissue of a plant may confer a phenotypic change. Alternatively, the expression of a sense or an anti-sense construct introduced into transgenic plants can cause the inhibition of expression of endogenous plant genes. This inhibition of expression can, in turn, produce the desired phenotypic change.

There is a need for a variety of different promoters to be used in the genetic engineering of plants. These promoters are of several types. Constitutive promoters are one such commonly used type of promoter. Constitutive promoters are those which are capable of expressing operably linked DNA sequences in all tissues of a plant throughout normal development. In contrast to constitutive promoters, tissue-specific promoters are those promoters that are capable of selectively expressing heterologous DNA sequences in certain plant tissues. Tissue-specific promoters may also be inducible, e.g., by application of external inducing agents. Constitutive and tissue-specific promoters are both used in the genetic engineering of plants, and have value for many different potential applications in this field.

Of particular interest to the present invention are tissue-specific promoters. These promoters can be fused with a heterologous DNA sequence and used to transform a plant cell to create transgenic plants that selectively express the heterologous DNA in a specific tissue. For example, the promoter regions from the fruit-specific, ethylene regulated genes E4 and E8 and from the fruit-specific polygalacturonase gene have been used to direct fruit specific expression of a heterologous DNA sequence in transgenic tomato plants. (See Cordes et al., *Plant Cell* (1989) 1;1025–1034, Deikman and Fischer, *EMBO J.* (1988) 7;3315–3320 and Della Penna et al., *Proc. Natl. Acad. Sci.* USA (1986) 83:6420–6424.)

The discovery of new tissue-specific promoters is desired for the controlled expression of various nucleic acid sequences that are genetically engineered into transgenic plants. There are many valuable potential applications of genetic engineering of plants. A variety of plant promoters with different characteristics and which are effective in different species of plants and/or organs is desirable in order to bring these potential applications into practice.

SUMMARY OF THE INVENTION

The present invention provides isolated plant P119 promoters containing a nucleic acid sequence that is either identical to or which has substantial sequence identity to the nucleic acid sequence depicted in SEQ. ID. No. 3. The P119 promoters of the invention are typically from a member of the family Solanaceae, for example, members of the genus Lycopersicon. A P119 promoter of the invention is typically from about 1200 nucleotides to about 2500 nucleotides in length. An example of such a promoter is the P119 promoter sequence contained in plasmid pG2.6XhoI(mut).

In addition to the above described promoter sequences, the present invention also provides for vectors and expression cassettes having a plant P119 promoter operably linked to a heterologous nucleic acid sequence. The heterologous nucleic acid sequence can encode a desired polypeptide or can be a sequence used to inhibit expression of an endogenous gene.

The present invention also provides for an isolated nucleic acid having a plant promoter operably linked to a nucleic acid sequence encoding a plant P119 protein. The plant P119 protein has an amino acid sequence that is either identical to or which has substantial sequence identity to the amino acid sequence depicted in Seq. ID No. 2. The nucleic acid encoding the P119 protein can have the nucleic acid sequence depicted in Seq. ID No. 1.

The present invention further provides transgenic plants comprising the expression cassettes of the invention. Methods for making plant cells comprising the expression cassette are also provided.

DEFINITIONS

The term "nucleic acids", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes self-replicating plasmids, infectious polymers of DNA or RNA and nonfunctional DNA or RNA.

In the polynucleotide notation used herein, unless specified otherwise, the left hand end of single-stranded polynucleotide sequences is the 5' end; the left hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "promoter" refers to a region of DNA upstream from the translational start codon and which is involved in recognition and binding of RNA polymerase and other proteins to initiate transcription. A "plant promoter" is a promoter capable of initiating transcription in plant cells.

The terms "P119 plant promoter" or "P119 promoter" as used herein refer to plant promoters having a nucleotide sequence identical to or substantially identical to some or all of SEQ. ID. No. 3. The promoters of the invention are typically derived from the P119 gene of tomato or other members of the Solanaceae family. Methods for determining nucleotide sequence identity are described below.

The term "tissue-specific promoter" as used herein refers to plant promoters that are capable of selectively expressing operably linked DNA sequences, in particular plant tissues.

This means that the expression of the operatively linked DNA sequences is higher in one or several plant tissues than it is in the other tissues of the plant. For example, the P119 promoters of the invention are tissue-specific promoters that express operably linked DNA sequences primarily in fruit tissue.

The term "operably linked" as used herein refers to linkage of a promoter upstream from a DNA sequence such that the promoter mediates transcription of the DNA sequence. It is understood that the promoter sequence also includes transcribed sequences between the transcriptional start and the translational start codon.

The phrase "expression cassette", refers to nucleotide sequences which are capable of affecting expression of a structural gene in hosts compatible with such sequences. Such cassettes include at least promoters and optionally, transcription termination signals. Additional factors necessary or helpful in effecting expression may also be used as described herein.

The term "vector", refers to viral expression systems and autonomous self-replicating circular DNA (plasmids). Where a recombinant microorganism, plant or cell culture is described as hosting an "expression vector," this includes extrachromosomal circular DNA or DNA that has been incorporated into the host chromosome(s), or both. Where a vector is being maintained by a host cell, the vector can either be stably replicated by the cells during mitosis as an autonomous structure, or incorporated within the host's genome.

The term "plasmid" refers to an autonomous circular DNA molecule capable of replication in a cell, and includes both the expression and nonexpression types. Where a recombinant microorganism or cell culture is described as hosting an "expression plasmid", this includes both extrachromosomal circular DNA molecules and DNA that has been incorporated into the host chromosome(s). Where a plasmid is being maintained by a host cell, the plasmid is either being stably replicated by the cells during mitosis as an autonomous structure or is incorporated within the host's genome.

A "heterologous sequence" or a "heterologous DNA sequence", as used herein, is one that originates from a foreign source (or species) or, if from the same source, is modified from its original form. Thus, a heterologous DNA encoding sequence operably linked to a promoter is from a source different from that from which the promoter was derived, or, if from the same source, is modified from its original form. Modification of the heterologous DNA sequence may occur, e.g., by treating the DNA with a restriction enzyme to generate a DNA fragment that is capable of being operably linked to the promoter. Modification can occur by techniques such as site-directed mutagenesis.

The phrase "selectively hybridizing to" refers to a nucleic acid probe that hybridizes, duplexes or binds only to a particular target DNA or RNA sequence when the target sequences are present in a preparation of total cellular DNA or RNA. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., *Molecular Cloning: A Laboratory Manual* (2nd ed.), Vols. 1–3, Cold Spring Harbor Laboratory, (1989) or *Current Protocols in Molecular Biology*, F. Ausubel et al., ed. Greene Publishing and Wiley-Interscience, New York (1987).

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length protein. For example, the term "a nucleic acid encoding a plant P119 protein" includes those nucleic acid sequences which encode non-full length amino acid sequences derived from the full-length P119 protein. It being further understood that the sequence includes the degenerate codons of the native sequence or sequences which may be introduced to provide codon preference in a specific host cell.

The phrase "isolated" or "substantially pure" when referring to nucleic acid sequences encoding P119 proteins, refers to isolated nucleic acids that do not encode proteins or peptides other than P119 proteins. When referring to P119 promoter sequences, the terms "isolated" or "substantially pure" refer to isolated nucleic acids that contain promoter sequences from a P119 gene, but which do not contain promoter sequences from other genes.

The term "plant" includes whole plants, plant organs (e.g., leaves, stems, roots, etc.), seeds and plant cells and progeny of same. The class of plants which can be used in the method of the invention is generally as broad as the class of higher plants amenable to transformation techniques, including both monocotyledonous and dicotyledonous plants. It includes plants of a variety of ploidy levels, including polyploid, diploid and haploid.

The term "transgenic plant" refers to a plant that has been produced by genetic engineering techniques. For example, plant cells transformed with vectors containing P119 promoters operably linked to heterologous DNA sequences can be used to produce transgenic plants with altered phenotypic characteristics.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as the nucleic acid sequence or may comprise a complete cDNA or gene sequence.

Optimal alignment of sequences for aligning a comparison window may be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci. (USA)* 85:2444, or by computerized implementations of these algorithms (GAP, BESTFIT, FASTA, and TFASTA in the Wisconsin Genetics Software Package Release 7.0, Genetics Computer Group, 575 Science Dr., Madison, Wis.).

The terms "substantial identity" or "substantial sequence identity" as applied to nucleic acid sequences and as used herein denote a characteristic of a polynucleotide sequence, wherein the polynucleotide comprises a sequence that has at least 85 percent sequence identity, preferably at least 90 to 95 percent sequence identity, and more preferably at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the P119 gene coding region or promoter regions, both disclosed herein.

As applied to polypeptides, the terms "substantial identity" or "substantial sequence identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more.

"Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to affect the properties of a protein. Examples include glutamine for asparagine or glutamic acid for aspartic acid.

DETAILED DESCRIPTION

Figure 1:
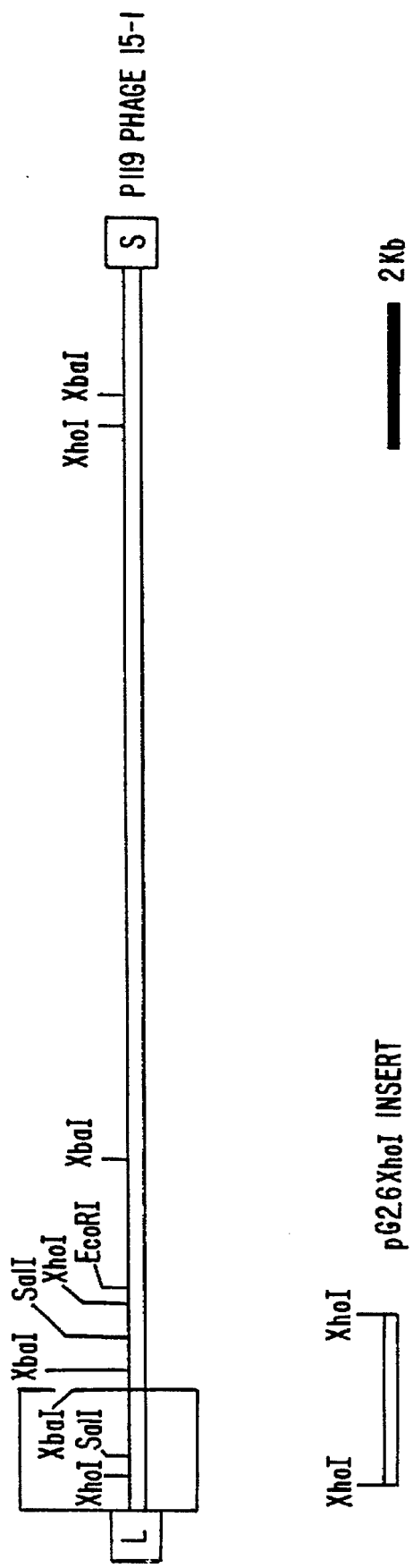
FIG. 1 is a restriction map of a genomic clone of a gene of the invention, phage 15-1.

This invention provides isolated plant P119 cDNA and genomic DNA constructs. It also provides isolated plant P119 promoters and DNA constructs containing a P119 promoter operably linked to heterologous DNA sequences. The promoters of the invention are tissue-specific and are useful in the production of transgenic plants. Desired phenotypes are produced in transgenic plants as a result of transformation of plant cells by a DNA construct containing heterologous DNA sequence operably linked to a P119 promoter.

A. Isolation of plant P119 promoters

This invention relates to isolated cDNA and genomic DNA molecules encoding plant P119 proteins. The invention also relates to isolated plant P119 promoters and recombinant DNA constructs containing the P119 promoter. These DNA constructs include expression cassettes and a variety of vectors.

1) cDNA and genomic DNA encoding plant P119 proteins

Nucleic acid sequences encoding plant P119 proteins are typically identical to or show substantial sequence identity (determined as described above) to the nucleic acid sequence encoding the tomato plant P119 protein depicted in SEQ ID. No. 1. (Seq. ID No. 1 is a cDNA sequence encoding a tomato plant P119 protein.) Nucleic acids encoding plant P119 proteins will typically hybridize to the nucleic acid sequence of Seq. ID No. 1 under stringent conditions. For example, high stringency hybridization can be done in buffer containing 50% formamide, 10% dextran sulfate, 10X Denhardts, 100 µg/ml salmon sperm, 1% SDS, 50 mM NaPO4, and 0.6M NaCl at 42° C. Filters are subsequently washed at 65° C. in 0.1X SSC, 0.1% SDS. Other stringent hybridization conditions may also be selected. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one.

Plant P119 proteins appear to form a multigene family in tomato plants. Plant P119 proteins typically show substantial sequence identity (as defined above) to the amino acid sequence of the tomato P119 protein as depicted in SEQ. ID. No. 2.

Techniques for nucleic acid manipulation of genes encoding plant P119 proteins such as subcloning nucleic acid sequences encoding polypeptides into expression vectors, labelling probes, DNA hybridization, and the like are described generally in Sambrook, et al., *Molecular Cloning—A Laboratory Manual* (2nd Ed.), Vol. 1–3, Cold Spring Harbor Laboratory, Cold Spring Harbor, N.Y., 1989. This manual is hereinafter referred to as "Sambrook, et al."

There are various methods of isolating DNA sequences encoding plant P119 proteins. For example, DNA is isolated from a genomic or cDNA library using labelled oligonucleotide probes having sequences complementary to the sequences disclosed herein (e.g., Seq. ID No. 1) Full-length probes may be used, or oligonucleotide probes may also be generated. Such probes can be used directly in hybridization assays to isolate DNA encoding plant P119 proteins. Alternatively, probes can be designed for use in amplification techniques such as PCR, and DNA encoding plant p119 proteins may be isolated by using methods such as PCR (see below).

To prepare a cDNA library, mRNA is isolated from a plant tissue which expresses a p119 protein. For instance, the pericarp tissue of the fruit of a plant can be used. cDNA is prepared from the mRNA and then a second, complementary DNA strand is synthesized. Subsequently, this duplex DNA molecule is ligated into a recombinant vector. The vector is transfected into a recombinant host for propagation, screening and cloning. Methods for making and screening cDNA libraries are well known. See Gubler, U. and Hoffman, B. J. *Gene* 25:263–269, 1983 and Sambrook, et al.

For a genomic library, typically the DNA is extracted from plant tissue and either mechanically sheared or enzymatically digested to yield fragments of about 15–20 kb. The fragments are then separated by gradient centrifugation from undesired sizes and are constructed in bacteriophage lambda vectors. These vectors and phage are packaged in vitro, as described in Sambrook, et al. Recombinant phage are analyzed by plaque hybridization as described in Benton and Davis, *Science*, 196:180–182 (1977). Colony hybridization is carried out as generally described in M. Grunstein et al. *Proc. Natl. Acad. Sci. USA.*, 72:3961–3965 (1975). DNA encoding plant p119 proteins is identified in either cDNA or genomic libraries by its ability to hybridize with nucleic acid probes, for example on Southern blots, and these DNA regions are isolated by standard methods familiar to those of skill in the art. See Sambrook, et al. See also Example 4, herein, for a description of the isolation of a pepper p119 gene.

In addition to screening using the sequences disclosed here, techniques designed to identify sequences specific to a particular tissue or cell types can be used to isolate sequences of the invention (see, e.g., Sambrook et al.) Such techniques include differential hybridization techniques as described in the example section or in Gurr et al. *Mol. Gen. Genet.* 226:361–366 (1991). Briefly, differential hybridization techniques can be used to identify root-specific genes using a cDNA library prepared from root cells. The library is screened with probes generated from cDNA derived from root cells and, for instance, leaf tissue. Those clones in the cDNA library which show increased hybridization to cDNA from root cells are candidates for genes which are preferentially expressed these cells. The clones identified in this way may then be used to screen a genomic library to isolate the corresponding gene.

In addition, subtractive hybridization techniques can be used to prepare specific probes for screening cDNA or genomic libraries. These techniques can also be used to prepare subtracted libraries enriched for the desired sequences. Subtractive screening or cDNA cloning approaches have proven effective in identifying transcripts with differential expression profiles. To ensure that cDNAs representing transcripts expressed in low abundance are represented requires that enough cDNA remain after subtraction for efficient cloning. Methods have been developed using PCR and other techniques to ensure that low abundance transcripts are identified.

The term "plant P119 gene" or "P119 gene" as used herein refers to a plant genomic DNA molecule that is the entire P119 promoter region operably linked to the entire coding region (including exons and introns) for the P119 protein and may include the adjacent 3' flanking region which encodes the 3' non-translated mRNA. The term "plant P119 gene fragment" or "P119 gene fragment" refers to a portion of the plant P119 gene which is less than the entire promoter and coding regions of the gene. A plant P119 gene fragment may be composed of a promoter region operably linked to a portion of the coding region of the gene.

Nucleic acid amplification techniques such as polymerase chain reaction (PCR) technology, can be used to amplify nucleic acid sequences encoding P119 proteins from mRNA, from cDNA, and from genomic libraries or cDNA libraries. In PCR techniques, oligonucleotide primers complementary to the two 3' borders of the DNA region to be amplified are synthesized. The polymerase chain reaction is then carried out using the two primers. See PCR Protocols: *A Guide to Methods and Applications* (Innis, M, Gelfand, D., Sninsky, J. and White, T., eds.), Academic Press, San Diego (1990). Primers can be selected to amplify the entire regions encoding a full-length P119 protein or its promoter. PCR can also be used to amplify smaller DNA segments of these regions as desired.

PCR and related amplification techniques can be used in a number of ways to isolate cDNA and DNA molecules encoding P119 proteins. For example, PCR can be used in a variety of protocols to isolate cDNAs encoding P119 proteins. In these protocols, appropriate primers and probes for amplifying DNA encoding plant P119 proteins are generated from analysis of the DNA sequences listed herein.

Oligonucleotides for use as primer or probes in the above-mentioned procedures can be chemically synthesized according to the solid phase phosphoramidite triester method first described by Beaucage, S. L. and Carruthers, M. H., 1981, *Tetrahedron Lett.,* 22(20):1859–1862 using an automated synthesizer, as described in Needham-VanDevanter, D. R., et al., 1984, *Nucleic Acids Res.,* 12:6159–6168. Purification of oligonucleotides is by either native acrylamide gel electrophoresis or by anion-exchange HPLC as described in Pearson, J. D. and Regnier, F. E., 1983, *J. Chrom.,* 255:137–149. The sequence of the synthetic oligonucleotide can be verified using the chemical degradation method of Maxam, A. M. and Gilbert, W. 1980, in Grossman, L. and Moldave, D., eds. Academic Press, New York, *Methods in Enzymology,* 65:499–560.

2) Plant P119 promoters

Plant P119 promoter sequences are typically identical to or show substantial sequence identity (determined as described above) to the tomato plant P119 promoter nucleic acid sequence depicted in SEQ ID. No. 3. Plant P119 promoter sequences typically hybridize to the nucleic acid sequence of Seq. ID No. 3 under stringent conditions, as described above.

Plant P119 promoters can be isolated in a variety of ways. Since P119 protein is a member of a multigene family, a number of different P119 promoters having homology or substantial sequence identity to the P119 promoter sequence of Seq. ID. No. 3 may be isolated from tomato plants. In addition, P119 promoters may be isolated from a variety of other plant species, in particular, other Solanaceae species.

There are a variety of methods known to those of skill in the art which may be used for isolation of plant P119 promoters. For example, plant P119 promoters can be isolated from genomic DNA fragments encoding a plant P119 protein and which also contain sequences upstream from the sequence encoding the P119 protein. Genomic fragments encoding plant P119 proteins can be isolated as described above. See Example 5, wherein, for a demonstration of the isolation of P119 promoter sequences from genomic DNA fragments which encode pepper P119 proteins.

Plant P119 promoter sequences can also be isolated by screening plant DNA libraries with oligonucleotide probes having sequences derived from the DNA sequence of the tomato P119 promoter of Seq. ID No. 3. The various methodologies described above for isolation of genomic DNA fragments encoding a P119 protein can also be used for the isolation of P119 promoters using the P119 promoter sequence of Seq. ID No. 3.

Other methods known to those of skill in the art can also be used to isolate plant DNA fragments containing P119 promoters. See Sambrook, et al. for a description of other techniques for the isolation of DNAs related to DNA molecules of known sequence. For instance, deletion analysis and a promoterless reporter gene (e.g., GUS) can be used to identify those regions which can drive expression of a structural gene. Sequences characteristic of promoter sequences can also be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions −80 to −100, there is typically a promoter element with a series of adenines surrounding the trinucleotide G (or T) N G. J. Messing et al., in *Genetic Engineering in Plants,* pp. 221–227 (Kosage, Meredith and Hollaender, eds. 1983).

Various modifications can be made to the promoters of the invention to provide promoters with different properties (e.g., tissue specificity, promoter strength, and the like). For instance, truncated forms of a P119 promoter can be constructed by mapping restriction enzyme sites in the promoter and then using the constructed map to determine appropriate restriction enzyme cleavage to excise a subset of the sequence. The modified promoters can then be inserted into a suitable vector and tested for their ability to drive expression of a marker gene. Tissue specificity of the modified promoters can be tested in regenerated plants.

The full length forms of a P119 promoter typically contain from 1,200 to 3,500 nucleotides. An example of a long form of a P119 promoter is one containing about 2,500 nucleotides.

B. Construction of vectors containing a P119 promoter operably linked to a heterologous DNA sequence Once a plant P119 promoter region has been isolated, various methods may be used to construct expression cassettes, vectors and other DNA constructs. A variety of techniques can be used for these manipulations of nucleic acids. These techniques are known to those of skill in the art and are described generally in Sambrook, et al., supra.

Expression cassettes containing a P119 promoter can be constructed in a variety of ways. For instance, various procedures, such as site directed mutagenesis can be used to introduce a restriction site at the start codon of a P119 gene fragment (see Example 5, herein). Then heterologous DNA sequences can be linked to the P119 promoter such that the expression of the heterologous sequences is regulated by the promoter. DNA constructs composed of a P119 promoter operably linked to heterologous DNA sequences can then be inserted into a variety of vectors. Such vectors include expression vectors that are useful in the transformation of plant cells. A variety of vectors useful in the transformation of plant cells can be constructed by the use of recombinant DNA techniques well known to those of skill in the art.

C. Production of transgenic plants

1) Use of DNA constructs containing P119 promoters to produce altered phenotypes in transgenic plants DNA constructs containing a P119 promoter operably linked to a heterologous DNA sequence can be used to transform plant cells and produce transgenic plants with desired phenotypic characteristics. There are a variety of different approaches one can use to produce a desired phenotype in transgenic plants. For example, by using methods described herein, one can operably link a heterologous gene to a P119 promoter and transform plant cells. Transgenic plants can be produced from the transformed plant cells so that the heterologous gene product is produced in certain tissues (e.g., fruit) of a transgenic plant. In this context, the term "heterologous gene" refers to a gene that is not normally present in a plant or which, if present, is not normally expressed in a particular plant cell tissue. The expression of the gene can result in the production of a protein that confers an altered phenotype on a transgenic plant.

A variety of genes capable of altering a plant phenotype can be expressed with a P119 promoter. Suitable genes include the following: genes for herbicide resistance; genes for fungal disease resistance (e.g., chitinases and glucanases); genes for bacterial disease resistance (e.g., cecropins); and genes for insect resistance (e.g., *B. thuringiensis* toxin). Since the P119 promoter provides tissue-specific expression, genes affecting fruit development are particularly useful. The P119 promoter can be used operably linked to, e.g., genes for ripening or degradation (e.g., Acc oxidase, Acc synthase, polygalacturonase, phytoene synthase); genes for color; or genes for sweetness.

One of skill will recognize that proteins have different domains which perform different functions. Thus, gene sequences operably linked to a P119 promoter need not be full length, so long as the desired functional domain of the protein is expressed. Modified protein chains can also be readily designed utilizing various recombinant DNA techniques well known to those skilled in the art. For example, the chains can vary from the naturally occurring sequence at the primary structure level by amino acid substitutions, additions, deletions, and the like. These modifications can be used in a number of combinations to produce the final modified protein chain.

DNA constructs containing a P119 promoter operably linked to a heterologous DNA sequence can also be used in a number of techniques to suppress expression of endogenous plant genes, e.g., sense or antisense suppression. In antisense technology, a nucleic acid segment from the desired plant gene is cloned and operably linked to a P119 promoter such that the anti-sense strand of RNA will be transcribed. The construct is then transformed into plants and the anti-sense strand of RNA is produced. In plant cells, it has been shown that anti-sense RNA inhibits gene expression; see, e.g., Sheehy et al., *Proc. Nat. Acad. Sci. USA*, 85:8805–8809 (1988), and Hiatt et al., U.S. Pat. No. 4,801, 340 which are incorporated herein by reference.

The nucleic acid segment to be introduced in antisense suppression generally will be substantially identical to at least a portion of the endogenous gene or genes to be repressed, but need not be identical. The vectors of the present invention can be designed such that the inhibitory effect applies to other proteins within a family of genes exhibiting homology or substantial homology to the target gene. Segments from a gene can be used (1) directly to inhibit expression of homologous genes in different plant species, or (2) as a means to obtain the corresponding sequences, which can be used to suppress the gene.

The introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments will be equally effective. Normally, a sequence of between about 30 or 40 nucleotides and about 2,000 nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes also have been reported to have use as a means to inhibit expression of endogenous plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozyme is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature,* 334:585-591 (1988), which is incorporated herein by reference.

A preferred method of suppression is sense suppression. Introduction of a nucleic acid configured in the sense orientation has been shown to be an effective means by which to block the transcription of target genes. For examples of the use of this method to modulate expression of endogenous genes see, Napoli et al., *The Plant Cell* 2:279-289 (1990), and U.S. Pat. No. 5,034,323, which are incorporated herein by reference. Sense suppression is a preferred method for ripening control (e.g., Acc oxidase or Acc synthase), sweetness control (e.g., ADPG pyrophosphorylase), or color modification (e.g., chalcone synthase); see U.S. Pat. No. 5,034,323.

Generally, in sense suppression, some transcription of the introduced sequence occurs. The effect may also occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity is useful to exert a more effective repression of expression of the endogenous sequences. Substantially greater identity of more than about 80% is preferred, though about 95% to absolute identity would be most preferred. The effect may be applied to other proteins within a similar family of genes exhibiting homology or substantial homology. Segments from a gene can be used (1) directly to inhibit expression of homologous genes in different plant species, or (2) as a means to obtain the corresponding sequences, which can be used to suppress the gene.

In sense suppression, the introduced sequence, needing less than absolute identity, also need not be full length, relative to either the primary transcription product or fully processed mRNA. A higher identity in a shorter than full length sequence compensates for a longer, less identical sequence. Furthermore, the introduced sequence need not have the same intron or exon pattern, and identity of non-coding segments may be equally effective. A sequence of a size of at least 50 base pairs is preferred, with greater length sequences being more preferred; see U.S. Pat. No. 5,034,323.

2) Transformation of plant cells and production of transgenic plants

Techniques for transforming a wide variety of higher plant species are well known and described in the technical and scientific literature. See, for example, Weising et al. *Ann. Rev. Genet.* 22:421-477 (1988). As described herein, a P119 promoter is operably linked to the desired heterologous DNA sequence in a suitable vector. The vector comprising a P119 promoter fused to heterologous DNA will typically contain a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta. Such elective marker genes are useful in protocols for the production of transgenic plants.

DNA constructs containing a P119 promoter linked to heterologous DNA can be introduced into the genome of the desired plant host by a variety of conventional techniques. For example, the DNA construct may be introduced directly into the genomic DNA of the plant cell using techniques such as electroporation and microinjection of plant cell protoplasts. Alternatively, the DNA constructs can be introduced directly to plant tissue using ballistic methods, such as DNA particle bombardment. In addition, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al., *Embo J.* 3:2717-2722 (1984). Electroporation techniques are described in Fromm et al., *Proc. Natl. Acad. Sci. USA* 82:5824 (1985). Ballistic transformation techniques are described in Klein et al., *Nature* 327:70-73 (1987).

Another method is high velocity ballistic penetration by small particles with the nucleic acid either within the matrix of small beads or particles, or on the surface (Klein et al., (1987) *Nature* 327:70-73. Although typically only a single introduction of a new nucleic acid segment is required, this method particularly provides for multiple introductions.

*Agrobacterium tumefaciens*-meditated transformation techniques are well described in the scientific literature. See, for example Horsch et al. *Science* (1984) 233:496-498, and Fraley et al. (1983) *Proc. Natl. Acad. Sci. USA* 80:4803. Typically, a plant cell, an explant, a meristem or a seed is infected with *Agrobacterium tumefaciens* transformed with the segment. Under appropriate conditions known in the art, the transformed plant cells are grown to form shoots, roots, and develop further into plants. The nucleic acid segments can be introduced into appropriate plant cells, for example, by means of the Ti plasmid of *Agrobacterium tumefaciens.* The Ti plasmid is transmitted to plant cells upon infection by *Agrobacterium tumefaciens,* and is stably integrated into the plant genome (Horsch et al., (1984) "Inheritance of Functional Foreign Genes in Plants," *Science,* 233:496-498; Fraley et al., (1983) *Proc. Nat'l. Acad. Sci. U.S.A.* 80:4803.

All plant cells which can be transformed by Agrobacterium and whole plants regenerated from the transformed cells can also be transformed according to the invention so as to produce transformed whole plants which contain the transferred foreign nucleic acid sequence.

There are various ways to transform plant cells with Agrobacterium, including:

(1) co-cultivation of Agrobacterium with cultured isolated protoplasts, (2) transformation of cells or tissues with Agrobacterium, or (3) transformation of seeds, apices or meristems with Agrobacterium.

Method (1) requires an established culture system that allows culturing protoplasts and plant regeneration from cultured protoplasts.

Method (2) requires (a) that the plant cells or tissues can be transformed by Agrobacterium and (b) that the transformed cells or tissues can be induced to regenerate into whole plants.

Method (3) requires micropropagation.

In the binary system, to have infection, two plasmids are needed: a T-DNA containing plasmid and a vir plasmid. Any one of a number of T-DNA containing plasmids can be used, the only requirement is that one be able to select independently for each of the two plasmids.

After transformation of the plant cell or plant, those plant cells or plants transformed by the Ti plasmid so that the desired DNA segment is integrated can be selected by an appropriate phenotypic marker. These phenotypic markers include, but are not limited to, antibiotic resistance, herbicide resistance or visual observation. Other phenotypic markers are known in the art and may be used in this invention.

The present invention embraces use of the claimed promoters in transformation of any plant, including both dicots and monocots. Transformation of dicots is described in references above. Transformation of monocots is known using various techniques including electroporation (e.g., Shimamoto et al., *Nature* (1992), 338:274–276; ballistics (e.g., European Patent Application 270,356); and *Agrobacterium* (e.g., Bytebier et al., Proc. Nat'l Acad. Sci. USA (1987) 84:5345–5349).

Transformed plant cells which are derived by any of the above transformation techniques can be cultured to regenerate a whole plant which possesses the desired transformed phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124–176, MacMillan Publishing Company, New York, 1983; and Binding, *Regeneration of Plants, Plant Protoplasts*, pp. 21–73, CRC Press, Boca Raton, 1985, all of which are incorporated herein by reference. Regeneration can also be obtained from plant callus, explants, organs, or parts thereof. Such regeneration techniques are described generally in Klee et al. *Ann. Rev. of Plant Phys.* 38:467–486 (1987).

One of skill will recognize that, after an expression cassette comprising the P119 promoter is stably incorporated in transgenic plants and confirmed to be operable, it can be introduced into other plants by sexual crossing. Any of a number of standard breeding techniques can be used, depending upon the species to be crossed.

The expression of the heterologous DNA sequences linked to a P119 promoter can be detected in a variety of ways, depending on the nature of heterologous sequences. For example, one may assay for the desired phenotype. The desired phenotype which results from the successful expression of heterologous DNA sequences under control of a P119 promoter may be determined by a variety of ways, depending on the phenotypic trait that is introduced. For instance, resistance to a herbicide can be detected by treatment with the herbicide.

Expression of the heterologous DNA can also be detected by measurement of the specific RNA transcription product. This can be done by, for example, RNAse protection or Northern blot procedures. If heterologous DNA sequences encode a novel protein, the protein product may be assayed, for instance, by its function or by a variety of immunoassay techniques. Alternatively, a novel protein product with enzymatic activity can be measured in an enzyme assay.

The methods and compositions of the invention have use over a broad range of types of plants, including species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Herecocallis, Nemesia, Pelargonium, Panicum, Pennisetum, Ranunculus, Senecio, Salpiglossis, Cucumis, Browaalia, Glycine, Lolium, Zea, Triticum, Sorghum, Datura, Chrysanthemum, Dianthus, Gerbera, Euphorbia, Ipomoea, Passiflora, Cyclamen, Malus, Prunus, Rosa, Rubus, Populus, Santalum, Allium, Lilium, Narcissus, Ananas, Arachis, Phaseolus and Pisum, and more particularly including oil crops such as canola (Brassica sp.), cotton (Gossypium sp.), peanut (Arachis sp.), sunflower (Helianthus sp.), palm (Elaeis sp.), flax (Linum sp.), safflower (Carthamus sp.), coconut (Cocos ap.) and soybean (Glycine sp.); grain crops such as wheat (Triticum sp.), corn (Zea sp.), sorghum (Sorghum sp.), barley (Hordeum sp.), rye (Secale sp.), oats (Avena sp.) and rice (Oryza sp.); fruit crops such as banana (Musa sp.), citrus (Citrus sp.), berries (e.g., strawberry (Fragaria Sp.) or raspberry (Rubus sp.), mango (Mangifera sp.), melon (Cucumis sp.), pear (Pyrus sp.), cucumber (Cucumis sp.), and apricot, peach, cherry, plum and prune (Prunus sp.); vegetable crops such as pea (Pisum sp.), bean (Vicia sp.), broccoli and related crucifers (Brassica sp.), spinach (spinacia sp.), onion (Allium sp.), celery (Apium sp.), carrot (Daucus sp.), asparagus (Asparagus sp.), and artichoke (Helianthus sp.); tomato (*Lycopersicon esculentum*), pepper (*Capsicum annuum*); additional ornamental crops such as tulip (Tulipa sp.), snapdragon (Antirrhinum sp.), Iris (Iris sp.), Orchids (Cymbidium and Cattleya sp.), pelargonium; beverage crops such as coffee (Coffea sp.) and tea (Thea sp.); herb crops such as mint (Mentha sp.), thyme (Thymus sp.) and marjoram (Origanum sp.).

The following examples are provided by way of illustration and not limitation.

EXAMPLES

Example 1: Isolation and characterization of P119 cDNA clones from cherry tomato plants P119 cDNA was obtained by the differential screening of a pink cherry tomato pericarp cDNA library with mature green and pink pericarp cDNA. Positive clones which also hybridized to leaf cDNA were eliminated. The selected cDNA clone was subsequently shown to hybridize strongly to tomato pericarp mRNA (from both mature green and various stages of ripening pericarp.) Moderate hybridization levels were seen with flower and developing fruit (immature green) mRNA, while low levels were seen with root and stem mRNA. No hybridization was seen with leaf mRNA.

Cherry tomato plants (*Lycopersicon esculentum* cv. Gold Nugget) were grown under green house conditions. Poly (A)$^+$ RNA was isolated from mature green fruit, pink fruit and leaf (Dunsmuir et al., eds., (1988) *Plant Molecular Biology Manual*, S. Gelvin and R. Schilperoovt, Kluwer Academic Dordrecht, pp. 1–17). Using the Lambda ZAP-cDNA synthesis kit (Stratagene), first strand cDNA was synthesized from the poly (A)+RNA (extracted from pink fruit) using oligo dT/(XhoI, SpeI) as the primer, methyl-C and reverse transcriptase. The second strand was synthesized using DNA polymerase I and RNAse H. The cDNA termini were blunted, then ligated to EcoRI linkers. The linkers were kinased, then the cDNA was digested with XhoI. Free linkers were separated from the cDNA using a Sephacryl spin column. The cDNA was then ligated to the Uni-Zap Arms and packaged in vitro using Gigapack packaging extracts (Stratagene).

40,000 recombinant phage from the pink fruit cDNA library (2000/85 mm plate) were plated using *E. coli* strain XL1-Blue. The phage plaques were transferred onto nitrocellulose filters (filters were made in triplicate) and the phage DNA was denatured in 1.5M NaCl, 0.5 N NaOH and neutralized in 1.5M NaCl, 0.5M Tris-HCl, pH8. The filters were screened with $^{32}$P radiolabeled cDNA made from pink fruit mRNA, mature green fruit mRNA and leaf mRNA. Hybridization conditions and washes were essentially as described in Sambrook, et al., supra.

Forty-five plaques were selected which hybridized strongly with immature green, mature green and pink pericarp cDNAs and not with leaf cDNA. DNA was purified from these selected phage for further analysis. The phage were induced to undergo in vivo auto-excision, producing phagemids (pBluescript SK–) for each clone.

The plasmid clones were first used in cross-hybridization experiments to determine if they were related to one another. 1–2 ug of digested plasmid DNA from the 45 clones was run in parallel on agarose gels, transferred to a nylon membrane (Duralon, Stratagene) and hybridized to random hexamer $^{32}$P labeled probes prepared from four of the cDNA clones of varying length. Southern transfer, probe preparation and hybridizations were done as described in Sambrook et al. Based upon the cross hybridization pattern the clones were placed into eight homology groups. Partial sequencing of one clone from each group gave 2 sets of sequence. One was already reported in the Genbank database, so clones hybridizing with this sequence were removed from the pool. Thirty-three clones remained, from which nine were selected for restriction mapping and partial sequencing.

The nine selected clones in vector pBluescript SK(–) (Stratagene) were sequenced using a combination of single and double-stranded templates. These clones were sequenced from both the 5' and 3' end by the Sanger dideoxy chain termination method. All 9 clones were found to be identical in primary sequence except for the position of the polyadenylation sites. A common feature of plant genes is that transcripts from a single gene will have variability in the polyadenylation site (see, Dean et al., *Nucl. Acid. Res.* 14:2229–2240 (1986)). These data suggest that the transcripts arise from a single gene. When the 9 clones were aligned according to each sequence, pP119 had the longest 3' sequence and pP28 had the longest 5' sequence. pP119 was completely sequenced. pP28 was sequenced across the 5' end which overlapped with pP119. The composite cDNA sequence is provided in SEQ. ID. No. 1.

The pP119 sequence was translated in three frames and the longest open reading frame (beginning with the first ATG) is provided in SEQ. ID. No. 2. The cloned cDNA fragment encodes a 110 amino acid polypeptide which is highly enriched in four amino acids (His, Lys, Ala, Glu). A comparison of the predicted protein sequence to sequences in EMBL Genbank shows homology to a protein encoded by the Asr1 gene (Iusem, et al., *Plant Physiology* 102:1353–1354 (1993)).

Example 2: Genomic DNA encoding P119 protein in fresh market tomato plants
Southern Hybridization Genomic Southern analysis was performed as described by Sambrook et al., 1989. Genomic tomato DNA was isolated from fresh market tomato (large fruited tomato) cultivar RG103-114 according to the method of Dooner et al., *Mol. Gen. Genet.* 200:240–246 (1985) and digested with HpaI, NcoI, BclI, EcoRI, HindIII, and XbaI. The digested DNA was separated on an agarose gel and transferred to Duralon membrane (Stratagene). The membrane was hybridized to $^{32}$P in vitro labeled RNA riboprobe prepared from pP119 (P119 cDNA clone). The hybridization patterns indicated that the P119 transcripts were derived from genes which were part of a small (at least two, maybe three member) multigene family in the tomato genome.

Example 3: Expression of P119 genes in cherry tomato plants

The P119 cDNA clone was used as a probe in Northern hybridizations to total RNA isolated from leaf, seed, stem, root, flower, and from pericarp tissue from immature green fruit, mature green fruit, pink fruit and red fruit. For Northern blots, 10 ug of total RNA was separated on a 1.5% agarose/formaldehyde gel and transferred to a nylon membrane. The Northern blots were prepared and hybridized to random hexamer $^{32}$P-labeled P119 cDNA as described in Sambrook et al., (1989). The cDNA clone was shown to hybridize strongly to tomato pericarp mRNA (from both mature green, pink and red pericarp.) Moderate hybridization levels were seen with flower and developing fruit (immature green) mRNA, while low levels were seen with root and stem mRNA. No hybridization was seen with leaf mRNA. See Table 1 below.

TABLE 1

Relative expression of P119 mRNA levels in tomato.

| Tissue | mRNA level | Tissue | mRNA level |
| --- | --- | --- | --- |
| Leaf | 1% | Fruit | |
| Stem | 2% | IG, 10 dpa | 20% |
| Root | 2% | IG, ½ size | 50% |
| Seed | 0 | MG | 100% |
| Flower | 20% | Pink | 100% |
| | | Red | 100% |

Example 4: Isolation of a gene from cherry tomato plants encoding P119 protein and containing the P119 promoter In order to isolate the genomic DNA region corresponding to the P119 gene, a genomic library was prepared from tomato DNA, and the P119 cDNA clone was used to screen the genomic library. The coding region from the cDNA was then aligned against the genomic region in order to identify the promoter region of the gene.

Tomato plants were grown in the greenhouse and nuclear DNA was isolated from young leaves as described in Dunsmuir, et al. *J. Mol. Appl. Genet.*, 2:285–300 (1983). The DNA was partially digested with Sau3A followed by partial fill-in of ends as described in the Lambda Fix II cloning kit manual (Stratagene). DNA in the 9–23 kb range was cloned into the XhoI (partially filled-in) site of the Lambda Fix II cloning vector (Stratagene) followed by in vitro packaging with Gigapack extracts (Stratagene) and plating in *E. coli* strain SRB. Five hundred thousand recombinant phage clones were screened (in duplicate) with two P119 probes: the full-length cDNA insert and the 5' EcoRI/PstI cDNA fragment. Each probe was hybridized to one set of filters. Thirty-four phage were isolated. Twenty-six of these phage hybridized only to the full-length probe. The remaining eight phage hybridized to both probes.

DNA was prepared from five of the phage which hybridized to both probes, and from one of the phage which hybridized to only the full-length probe. The DNA's were digested with EcoRI, SalI, XbaI and XhoI in order to generate restriction maps. The clones overlap and appear to be derived from a single genomic region. The restriction map of phage 15-1 is shown in FIG. 1 as an example.

Hybridization of the P119 full-length cDNA probe to the phage DNAs localized the P119 coding region as shown in FIG. 1 by a boxed area. Subsequent hybridization with the grp1-PE oligo (located at the 5' end of the cDNA), allowed orientation of the fragments with respect to the 5' and 3' ends of the cDNA. The hybridization patterns indicated that the XhoI and SalI sites clustered at one end of the phage corresponded to the 5' end of the cDNA. This implied that most of the phage carried 5' untranslated (promoter) region. A subclone was prepared using the hybridizing 2.6 kb XhoI fragment from phage 15-1 (see, FIG. 1). This fragment, which included a small portion (80 bp) of the P119 coding sequence and approximately 2.5 kb of 5' noncoding sequences, was subcloned into the XhoI site of pBluescript II KS(+) (Stratagene, San Diego, Calif., USA) to give plasmid pG2.6XhoI.

Figure 2:
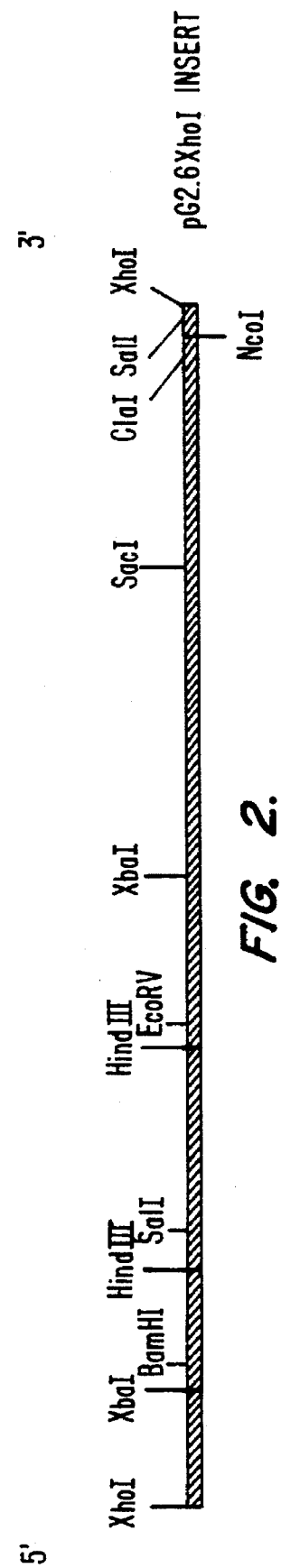
FIG. 2 is a restriction map of a promoter of the invention.

In order to generate a more detailed restriction map of the subcloned region, pG2.6XhoI plasmid DNA was digested with the enzymes SacI, XbaI, BamHI, HindIII, SalI and EcoRV (FIG. 2). Precise localization of the P119 gene coding region within this fragment was achieved by sequence analysis of the two ends of the subcloned fragment and alignment of these sequences with the known P119 cDNA sequence.

There was complete agreement between the sequences of the genomic region containing the XhoI/SalI cluster and the cDNA clone. The region sequenced corresponded to 119 bp of the 5' end of the cDNA, including 29 bp of untranslated sequences and 90 bp of coding region. These data indicated that the genomic region cloned in phage 15-1 is the genomic equivalent of the P119 cDNA and that the P119 transcripts present in fruit derive from this gene. Hence the DNA from pG2.6XhoI was used for the promoter isolation and preparation of an expression cassette.

Example 5: Preparation of an expression cassette containing a long form of the p119 promoter A long P119 promoter was produced using the P119 promoter region contained in the pG2.6XhoI clone. Site directed mutagenesis was used in order to introduce a restriction site at the translation start codon for the P119 protein. The restriction site at the position of the translation start facilitates fusions to this promoter. The sequences surrounding the translation start of the P119 coding region were mutagenized (according to the method of Kunkel (1985) *Proc Natl Acad Sci* 82: 488–492) in order to introduce a NcoI site. The oligonucleotide which was used for this purpose is shown below:

5'-TGTTTCCCATGGAGGAGGAG-3'     (SEQ. ID. No. 4)
       NcoI

The mutant clone pG2.6XhoI(mut) was subsequently used as the source of the P119(Long) promoter fragment.

The sequence of tomato genomic DNA in the pG2.6XhoI clone was determined by the Sanger dideoxy method and is shown in SEQ. ID. No. 3. The sequence is identical to the sequence of the cDNA clone in the regions which they have in common, namely the transcriptional leader in the cDNA and the 5' end of the coding region up to the XhoI site.

Example 6: Production of vectors containing a long form of the P119 promoter and a short form of the p119 promoter operably linked to the ChiA gene The long form of the P119 promoter produced in Example 5 was operably linked to the ChiA gene, in order to examine the expression of DNA sequences linked to this form of the promoter. The enzymes NcoI and EcoRI were used to isolate the long promoter fragment from the pG2.6XhoI(mut) plasmid. This fragment was ligated into a chitinase expression vector p2104-cabL, (Harpster et al., (1988), *Molecular and Gen. Genetic*, 212:182–190) from which the CaMV 35S promoter had been removed via digestion with NcoI and EcoRI. The resultant expression vector was named P119L/ChiA and was composed of the long P119 promoter, the ChiA coding region and the NOS 3' sequence.

The P119L/ChiA expression cassette was inserted into the binary vector pWTT2132. WTT2132 is a binary vector containing the following components: the tetracycline resistance (tetR) gene, fragments containing the replicon from pACYC184 (Chang and Cohen (1978) *J. Bacteriol* 134: 1141–1156) and pVSI (Itoh et al., (1984) *Plasmid* 11: 206–220). In addition there is the 35SCab22L promoter (Harpster et al., (1988), *Molecular and Gen. Genetic*, 212:182–190) fused to the tobacco surB gene (Lee et al., (1988), supra), and the lacZa fragment of the B-galactosidase gene (Yanisch-Perron et al., (1985) *Gene* 33: 103–119) located between the left and right T-DNA borders from the *A. tumefaciens* octopine Ti-plasmid (van den Elzen et al., (1985) *Plant Mol Biol* 5: 149–154).

The plasmid P119L/ChiA was digested with EcoRI, the ends were filled in, and the DNA was then digested with PstI. This blunt/PstI fragment was ligated to SmaI/PstI-digested pWTT2132 plasmid. The short version of the promoter linked to ChiA (P119S/ChiA) was produced by digesting the P119L/ChiA plasmid with HindIII and isolating the 3.3 kb fragment carrying 1.3 kb of the P119 promoter, the ChiA gene and the NOS 3' sequences. The ends of this fragment were filled in and it was ligated to SmaI cut pWTT2132 binary vector. This gave clones in both orientations. A clone was chosen which had the same orientation as P119L/ChiA in the binary (NOS 3' sequences next to the right border.)

The newly formed binary vectors WTT2132/P119L-ChiA and WTT2132/P119S-ChiA were transferred by triparental mating with *E. coli* strain HB101/pRK2013 (Figurski and Helinski (1979) *Proc Natl Acad Sci* 76:1648–1652) into the *A. tumefaciens* strain LBA4404 (Hoekema et al., (1983) *Nature* 303: 179–180) which contains the virulence region of the Ti plasmid.

Example 7: Transformation of cherry tomato plants with a vector containing a short and a long form of the P119 promoter operably linked to the ChiA gene 1) Preparation of an Agrobacterium strain carrying the pWTT2132/P119L-ChiA and the pWTT2132/P119S-ChiA plasmid Fresh cultures of *A. tumefaciens* LBA 4404 harboring plasmid pAL4404 were grown at 28° C. for 24 h from a single colony in minimal A. *E. coli* HB101 containing the plasmid pRK2013 and *E. coli* HB101 containing the pWTT2132/P119L-ChiA and the pWTT2132/P119S-ChiA plasmids prepared as described in Example 6 were grown for 6 hours in L broth. For triparental mating, 0.5 ml of the *A. tumefaciens* culture were mixed on the same LB agar plate with 0.25 ml of HB101/pRK2013 and 0.25 ml of HB101/pWTT2132/P119L-ChiA or /pWTT2132/P119S-ChiA and the plates were incubated for 24 hours at 28° C. A loopful of bacteria from each plate was then resuspended in 1 ml minimal A and plated at $10^0$, $10^{-2}$ and $10^{-4}$ dilutions on LB plates containing 100 µg/ml rifampicin and 1 µg/ml tetracycline. After several days growth at 28° C., individual colonies were restreaked onto minimal A plates containing 1 µg/ml tetracycline. Subsequently the Agrobacterium strain which carried the transferred plasmids were used in the transformation of tomato.

2) Transformation of cherry tomato plants

All manipulations were carried out under sterile conditions. A culture of Agrobacterium LBA4404 containing the pWTT2132/P119L-ChiA plasmid or the pWTT2132/P119S-ChiA plasmid was grown for 24 hours in minimal A medium at 28° C. Explants were excised from the midsections of 7–8 day old cotyledons of *L. esculentum* seedlings grown sterilely on germination medium. The Agrobacterium culture was diluted in liquid 2% glucose-OMS to a final concentration of $5 \times 10^5$ cfu/ml.

The explants were submerged in the Agrobacterium suspension for 20–30 minutes and then placed on cocultivation plates for 2 days at 25° C. The cocultivation was terminated by washing the leaf discs in liquid 2% glucose-OMS for 2 hours. The explants were then placed on solid regeneration media and cultured under high light fluence with an 8 hour dark period at 25° C. After 10 days, kanamycin resistant callus appeared and then small shoot buds by 3 weeks. At 5 weeks the healthy calli and shoots were transferred to fresh selection regeneration medium and within 2 weeks many transformed shoots emerged. The shoots were then excised and transferred to selective rooting medium. Plants that successfully developed shoots in this medium in 6–10 days were all transformants. These plants were then transferred to non-selective rooting medium for 2 weeks to check for residual Agrobacterium, then transplanted to soil.

Example 8: Measurement of ChiA gene expression in transformed cherry tomato plants An advantage of using the chitinase marker gene is that it is feasible to measure either RNA levels or enzyme activity in order to monitor promoter activity. In this example, chitinase activity levels were measured qualitatively using the substrate 4-methyl umbelliferone. The RNA levels were then measured by the primer extension method.

Chitinase activity levels were determined using a microtiter plate assay. Tissues were frozen in liquid nitrogen, then ground to a fine powder with a mortar and pestle. Extraction buffer containing 100 mM Tris (pH 8), 150 mM 2-mercaptoethanol and various protease inhibitors was added to the frozen powder and mixed in as the tissue thawed. The extract was ground until soupy. Extracts were transferred to microfuge tubes and the debris was spun out. The protein concentration of the extract supernatant was determined and the assay performed with equal amounts of protein from each sample. 20–50 ug of protein (in a 50 ul volume) was mixed with an equal volume of 0.05 mg/ml $(Glc-Nac)_3$-Methyl-umbelliferone in a 96-well microtiter dish. The reaction was allowed to proceed at room temperature for 1 hour. Active chitinase results in brilliant blue fluorescence when the plate is exposed to medium/long wave UV.

For the plants transformed with P119L/ChiA, 50 ug of total protein extract from tomato leaf or mature green pericarp tissue were assayed. 19 independent primary transformants were assayed. All plants showed no detectable activity in leaf tissue. 15 plants showed variable levels of expression in mature green pericarp tissue, while the remaining 4 plants showed no activity in this tissue (see Table 2.) For the plants transformed with P119S/ChiA, 20 ug of total protein extract were assayed (also from leaf and mature green pericarp.) 23 independent primary transformants were assayed. All plants showed no detectable activity in leaf tissue. 22 plants showed variable levels of expression in mature green pericarp tissue, while the remaining 1 plant showed no activity in this tissue (see Table 3.)

For Tables 2–6 below, the measurements are recorded on the following ascending 6-step scale (with approximately equal intervals between steps): –, (+), +, ++, +++,++++ with the first step (dash) being not detected and the last step (quadruple plus) being highest level.

TABLE 2

Measurement of chitinase activity levels in transgenic tomato transformed with P119L/ChiA

| TRANS # | LEAF | FRUIT | Notes |
| --- | --- | --- | --- |
| 1401 | — | + | |
| 1402 | — | ++ | |
| 1403 | — | — | |
| 1404 | — | ++ | |
| 1405 | — | ++ | |
| 1406 | — | — | |
| 1407 | — | (+) | |
| 1408 | — | +++ | |
| 1409 | — | +++ | |
| 1410 | — | ++ | |
| 1411 | — | +++ | |
| 1412 | — | ++ | |
| 1413 | — | ++ | |
| 1414 | — | — | |
| 1415 | — | +++ | |
| 1416 | — | — | |
| 1417 | — | + | |
| 1419 | — | + | |
| 1420 | — | + | red fruit used |
| B001 | — | — | empty vector transformant |
| BEBC | — | — | non-transformed plant |

TABLE 3

Measurement of chitinase activity levels in transgenic tomato transformed with P119S/ChiA

| TRANS # | LEAF | FRUIT | Notes |
| --- | --- | --- | --- |
| 1501 | — | ++ | |
| 1502 | — | + | |
| 1503 | — | ++ | |
| 1505 | — | — | |
| 1506 | — | +++ | |
| 1507 | — | +++ | |
| 1508 | — | (+) | orange fruit used |
| 1509 | — | +++ | |
| 1510 | — | +++ | |
| 1511 | — | ++ | |
| 1512 | — | +++ | |
| 1513 | — | ++ | |
| 1514 | — | ++ | |
| 1516 | — | + | |
| 1517 | — | ++ | |
| 1518 | — | + | |
| 1519 | — | ++ | |
| 1520 | — | (+) | |
| 1523 | — | (+) | |
| 1524 | — | ++ | |
| 1525 | — | ++ | |
| 1526 | — | +++ | |
| 1527 | — | ++ | |
| B001 | — | — | empty vector transformant |
| BEBC | — | — | non-transformed plant |

Primer extensions were subsequently done to quantitate the level of RNA in leaf and fruit tissues of the transgenic plants. 10 ug of total RNA from leaf and red pericarp tissues were analyzed, using a 18 bp oligonucleotide positioned 97 bp downstream of the translation start in the ChiA gene. The sequence of the primer which was used is shown below:

5'-CGAACTTGGTGTTGCCCC-3'  (SEQ. ID. No. 5)

Using the primer extension assay ChiA mRNA was detected in P119L/ChiA plants in fruit and occasionally in leaf tissue. The expression level was always higher in fruit than in leaf. See Table 4 below. Primer extensions were also used to detect ChiA mRNA in the P119S/ChiA transformants.

Again, expression was seen in fruit and occasionally at a low level in leaf tissue. See Table 5 below.

TABLE 4

Measurement of ChiA mRNA levels in transgenic tomato transformed with P119L/ChiA

| TRANS # | LEAF | FRUIT |
|---|---|---|
| 1401 | − | (+) |
| 1402 | (+) | ++ |
| 1403 | − | − |
| 1404 | (+) | ++ |
| 1405 | − | + |
| 1406 | − | − |
| 1407 | − | − |
| 1408 | (+) | ++ |
| 1409 | + | +++ |
| 1410 | − | ++ |
| 1411 | (+) | ++ |
| 1412 | (+) | +++ |
| 1413 | + | ++ |
| 1414 | − | − |
| 1415 | − | ++ |
| 1416 | − | + |
| 1417 | (+) | (+) |
| 1419 | (+) | ++ |
| 1420 | (+) | ++ |

TABLE 5

Measurement of ChiA mRNA levels in transgenic tomato transformed with P119S/ChiA

| TRANS # | LEAF | FRUIT |
|---|---|---|
| 1501 | − | ++ |
| 1502 | − | (+) |
| 1503 | − | ++ |
| 1505 | − | − |
| 1506 | (+) | ++ |
| 1507 | − | ++ |
| 1508 | − | + |
| 1509 | (+) | +++ |
| 1510 | − | ++ |
| 1511 | − | ++ |
| 1512 | − | + |
| 1513 | − | + |
| 1514 | − | (+) |
| 1516 | − | ++ |
| 1517 | − | + |
| 1518 | − | ++ |
| 1519 | − | +++ |
| 1520 | − | ++ |
| 1523 | − | +++ |
| 1524 | − | ++ |
| 1525 | − | ++ |
| 1526 | (+) | +++ |
| 1527 | (+) | ++ |

Example 9: Transformation of fresh market tomato plants with a vector containing a long form of the P119 promoter operably linked to the AccS gene The P119L promoter was operably linked to a truncated version of the tomato ACC synthase gene (AccS) and transformed into tomato plants. Two previously existing constructs were used to create an expression cassette carrying P119 and AccS. p35S/AccS and P119L/ChiA were both digested with NcoI and PstI (located adjacent to the HindIII site of the NOS3' sequences in both clones.) A 1.4 Kb fragment containing the AccS/NOS3' sequences and a ~5.4 Kb fragment containing the P119 promoter and pUC vector sequences were gel purified and subsequently ligated together to form P119L/AccS. An EcoRI partial digest, followed by a complete PstI digest was done on the pP119L/AccS plasmid and the ends were made flush with T4 Polymerase. The resultant ~3.7 Kb blunt-ended fragment containing the P119L/AccS/NOS3' fusion was isolated and cloned into the SmaI site of the binary vector pWTT2179. The tomato transformation protocol described above was then used to produce transgenic plants comprising the expression cassette.

Example 10: Measurement of AccS gene expression in transformed fresh market tomato plants The Acc2 full-length cDNA clone was used as a probe on Northern blots for expression of the AccS transgene in six randomly chosen plants from the D13000 series (P119L/AccS) of transgenic tomato plants. For comparison, three 35S/AccS (A11000) plants with varying levels of AccS transgene expression were included. For Northern blots, 10 ug of total RNA from leaf or pink fruit was separated on a 1.5% agarose/formaldehyde gel and transferred to a nylon membrane. The Northern blots were prepared and hybridized to random hexamer $^{32}$P-labeled Acc2FL cDNA as described in Sambrook et al., (1989), supra. See Table 6 below.

TABLE 6

Levels of AccS mRNA in tomato plants transformed with the P119L/AccS gene

| TRANS # | LEAF | FRUIT |
|---|---|---|
| A010 | NA | (−) |
| A11012 | NA | ++ |
| A11054 | NA | (+) |
| A11077 | NA | +++ |
| D11006 | (−) | ++ |
| D11013 | (−) | + |
| D11015 | (−) | + |
| D11017 | (−) | + |
| D11025 | (−) | ++ |
| D11027 | (−) | ++ |

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A composition comprising an isolated nucleic acid molecule comprising a tomato plant P119 promoter.

2. The composition of claim 1, wherein said promoter comprises a nucleic acid sequence identical to Seq. ID No. 3.

3. The composition of claim 1, wherein said promoter is from about 1200 to about 2500 nucleotides in length.

4. The composition of claim 1, wherein said promoter is contained in plasmid pG2.6XhoI(mut).

5. A vector comprising a tomato plant P119 promoter operably linked to a heterologous nucleic acid sequence.

6. The vector of claim 5 wherein said P119 promoter comprises a nucleic acid sequence identical to Seq. ID No. 3.

7. The vector of claim 5, wherein said P119 promoter is the P119 promoter of plasmid pG2.6XhoI (mut).

8. An expression cassette comprising a tomato plant P119 promoter operably linked to a heterologous nucleic acid sequence.

9. The expression cassette of claim 8, wherein said P119 promoter comprises a nucleic acid sequence identical to Seq. ID No. 3.

10. A transgenic plant comprising a tomato plant P119 promoter operably linked to a heterologous nucleic acid sequence.

11. The transgenic plant of claim 10, wherein said P119 promoter comprises a nucleic acid sequence identical to Seq. ID No. 3.

12. The transgenic plant of claim 10, wherein said plant is a member of the family Solanaceae.

13. The transgenic plant of claim 10, wherein said plant is a tomato plant.

14. A method of expressing a heterologous nucleic acid sequence in a plant cell comprising:

a) transforming said plant cell with a vector comprising a tomato plant P119 promoter operably linked to the heterologous nucleic acid sequence; and b) growing said plant cell under conditions where the heterologous nucleic acid sequence is expressed in said plant cell.

15. The method of claim 14, wherein said P119 promoter has the nucleotide sequence depicted in Seq. ID No. 3.

16. The method of claim 14, wherein said P119 promoter is the P119 promoter contained in plasmid pG2.6XhoI (mut).

17. The method of claim 14, wherein said plant cell is from a member of the family Solanaceae.

18. The method of claim 14, wherein said plant cell is a tomato plant cell.

19. The method of claim 14, wherein said plant cell is a tomato plant cell.

20. The method of claim 14, wherein said plant cell is a tobacco plant cell.

21. An isolated nucleic acid molecule comprising a promoter sequence of about 2500 nucleotides, which promoter sequence hybridizes to SEQ. ID. No. 3 under hybridization conditions which include washing at 65° C. in 0.1X SSC, 0.1% SDS.

22. The isolated nucleic acid molecule of claim 21, wherein the promoter sequence is SEQ. ID. No. 3.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

(i) SEQUENCE CHARACTERISTICS:
  (A) LENGTH: 730 base pairs
  (B) TYPE: nucleic acid
  (C) STRANDEDNESS: single
  (D) TOPOLOGY: linear (ii) MOLECULE TYPE: cDNA (ix) FEATURE:
  (A) NAME/KEY: misc_feature
  (B) LOCATION: 1..730
  (D) OTHER INFORMATION: /standard_name= "P-119 cDNA"

(ix) FEATURE:
  (A) NAME/KEY: CDS
  (B) LOCATION: 30..359

(xi) SEQUENCE DESCRIPTION: SEQ ID NO:1:

```
CTAAATTATC GATAGATTTA TTGTTTCAG ATG GAG GAG GAG AAA CAC CAC CAC          53
                               Met Glu Glu Glu Lys His His His
                                 1               5

CAC CAC CTG TTC CAC CAC AAG GAC AAG GCG GAG GAG GGC CCC GTC GAC         101
His His Leu Phe His His Lys Asp Lys Ala Glu Glu Gly Pro Val Asp
         10                  15                  20

TAC GAA AAA GAA ATC AAA CAC CAT AAA CAT CTC GAG CAA ATC GGT AAA         149
Tyr Glu Lys Glu Ile Lys His His Lys His Leu Glu Gln Ile Gly Lys
 25                  30                  35                  40

CTT GGC ACT GTT GCT GCC GGT GCC TAC GCC TTG CAT GAG AAA CAT GAG         197
Leu Gly Thr Val Ala Ala Gly Ala Tyr Ala Leu His Glu Lys His Glu
                 45                  50                  55

GCA AAG AAA GAT CCA GAA CAT GCA CAC AAA CAC AAG ATA GAG GAA GAG         245
Ala Lys Lys Asp Pro Glu His Ala His Lys His Lys Ile Glu Glu Glu
                 60                  65                  70

ATA GCA GCA GCT GCT GCA GTT GGG GCA GGT GGA TTT GCA TTC CAT GAG         293
Ile Ala Ala Ala Ala Ala Val Gly Ala Gly Gly Phe Ala Phe His Glu
                 75                  80                  85

CAT CAT GAG AAA AAA GAT GCC AAG AAA GAA GAA AAA AAA GCT GAG GGG         341
His His Glu Lys Lys Asp Ala Lys Lys Glu Glu Lys Lys Ala Glu Gly
         90                  95                 100

GGA CAC CAC CAT CTC TTC TAAATTGTTA TTTTAGTTAC ATTTTAATA                 389
Gly His His His Leu Phe
105             110

TTCGTGGAAT TCCATATTT GGTATAAGTG TTGTGTCATC TTATCATATA TCGTGCATAA        449

TAACAATAAA TTAGTGTGA TATTATAAAT GGATCGAGTT AAAAAAAAAG AGCAAAAGTC        509

AAAATATATT TTACCAATCT CGTGTGATGT AAAGAAGGAT GTATTGTGAT TTCCAAAATG      569

ATCATGTGTG TTTTGGACTT TCCTCGCAAT CTTCTGTTGA ATTACCTTGT AAAATGTTGC      629

TTTTTAAGT GGTGTAATAA ATAATGAGTT TTCTAGTGAA TGGATTTGTT TGATTTCCTA       689

AATAATGATG TTTTTTTTTT TTAAAAAAAA AAAAAAAAA A                            730
```

(2) INFORMATION FOR SEQ ID NO:2:

(i) SEQUENCE CHARACTERISTICS:
    (A) LENGTH: 110 amino acids
    (B) TYPE: amino acid
    (D) TOPOLOGY: linear (ii) MOLECULE TYPE: protein (xi) SEQUENCE DESCRIPTION: SEQ ID NO:2:

```
Met Glu Glu Glu Lys His His His His His Leu Phe His His Lys Asp
 1               5                  10                  15

Lys Ala Glu Glu Gly Pro Val Asp Tyr Glu Lys Glu Ile Lys His His
```

|   |   | 20 |   |   | 25 |   |   |   | 30 |   |   |   |
|---|---|---|---|---|---|---|---|---|---|---|---|---|

Lys His Leu Glu Gln Ile Gly Lys Leu Gly Thr Val Ala Ala Gly Ala
         35                  40                   45

Tyr Ala Leu His Glu Lys His Glu Ala Lys Lys Asp Pro Glu His Ala
         50                  55                   60

His Lys His Lys Ile Glu Glu Glu Ile Ala Ala Ala Ala Ala Val Gly
 65                      70                   75                  80

Ala Gly Gly Phe Ala Phe His Glu His His Glu Lys Lys Asp Ala Lys
              85                       90                   95

Lys Glu Glu Lys Lys Ala Glu Gly Gly His His His Leu Phe
             100                 105                 110

(2) INFORMATION FOR SEQ ID NO:3:

(i) SEQUENCE CHARACTERISTICS:
      (A) LENGTH: 2454 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: misc_feature
      (B) LOCATION: 1..2454
      (D) OTHER INFORMATION: /standard_name= "P-119 PROMOTER"

(ix) FEATURE:
      (A) NAME/KEY: misc_feature
      (B) LOCATION: 2452..2454
      (D) OTHER INFORMATION: /note= "Translation start codon for
          P-119"

(xi) SEQUENCE DESCRIPTION: SEQ ID NO:3:

| | | | | | |
|---|---|---|---|---|---|
| CTCGAGTCCA | TTGTGGGGCT | CCCATTTCTC | TTTGCATTTC | AAGAGGGAGC | CATAAAGGCT | 60 |
| CTAAATGTCA | TTCATCGAGT | CAATTCGTCA | AAATCGGCGT | ATGAAGTCAA | ATTTCAAAGT | 120 |
| TTAGGAGATT | GAAGAAATTT | GAAGAAGACT | AACTAGAAGA | CTTCTTTAGT | TTTTTTTTA | 180 |
| TATTTTGTGT | TTCTTTTGTA | ATGGCCTAAG | CCCTTATGGT | TTTATTTTCT | TGTACCTATT | 240 |
| CTTGTATGTC | TAGACTAGGA | CAGGTACAAA | AGAAAGAAAT | GGGTCGAAAA | TCCAAAAAAC | 300 |
| AGGCGGATCC | AAAACTTGGT | CAAGGCGAAC | AGAACCTGAG | TTTGGACCCA | AATCTCTCTC | 360 |
| TCTCACTTTA | CTATTTGTTT | ACGTATTTTT | GCTTAAATGT | CGTTAGCTTA | GGATTAGAAA | 420 |
| CTCCAAACCC | CGTCGAACGC | CTTTTAAATT | TTCGTCAAAC | TTAAAATTAA | CTTTTTAACG | 480 |
| ATAATTTGTT | TCAAATTTGC | AAAGCTTGTT | AGATAAAACC | TTAGGAAAGT | TTAACTTTGA | 540 |
| AATAGATTCG | CAAAATTGTG | AAATAAACAA | TAAAGATTGC | AAAACTTGTC | GACTTGTTTA | 600 |
| AATGAAATAA | AAGTTCAACT | TCAAATTGCA | AAAGTTACAA | AAAATAGTCA | AATAAGTTAA | 660 |
| TCGCCGGAAA | ATCGTATTTA | ACGGAGTGTC | ACCTTCCTAA | GACACTAATA | GGAATCCCGA | 720 |
| ACTCTTTAAC | ATTTTCCAAA | CAATTTTCCT | GTTTTAAAGT | TGTTTAGAAA | ATAAGTTTTC | 780 |
| TTAATTTTCT | CAAAATTAAG | TGGCGACTCC | TAAAAAGTCG | AAAATCCTCT | GAGATAAAAC | 840 |
| AAACTCTTTT | CGAAAATCAT | TTTTTTCGAT | AAAACAAAAT | AAATTAAAAT | GAATAGAAAG | 900 |
| AAAAGTTAAA | ACAGTGGGAG | TACTAAGAAT | TGTATGCGTC | TATATCTTTT | TTTTATATCA | 960 |
| TTTAACTTAG | TGGTACAAGC | TTTCTGCCTA | TTATATAGAA | CGAGTAAGCG | CCATTTGTTG | 1020 |
| CAAGATATCT | TTTTATAACA | AAATACAAGT | TAATTTTCAG | ATTAAAAAAT | ATTTAAGAAG | 1080 |
| TTTTTGAAAA | GGGAGTTACA | TGAATTTTAT | TATTTTAGGA | GTTAATAACT | TAGTTACACT | 1140 |
| TTAGTTTGTA | ATATTAAATA | TTTTATTAAA | TTTGGTGCC | CCAAAGACGT | CCAAATACAT | 1200 |

```
GTTACTTGAG  GTCAAATTTA  AGTGTAATTT  GAAAAAAAA   AGATCGTTGT  AACCAAGTGT   1260
ATTAGCATAT  ATTTAGGATA  CATAGTAAAT  CTCCTTCACC  TCTTTCCCAT  CTTGCTTGCC   1320
ACTCTCTCGT  ATATCTAATA  TTCTAGATAC  ATGTGAATCA  CTCCTGATAT  ATGTACATAG   1380
TTTGATTCAC  ATAATATATG  TATAGGATAC  ATACAAATTT  CACTTGTTTT  TTTTTCTATT   1440
TTTTGTGTAT  CACGTAACAA  AAATATATAT  ATCTCAGTGT  AGAATACATA  AAAAAAATTT   1500
TAATTAGTGA  TAAAATATAT  AATATGATTA  AAAATATAAA  TAATAATAAT  ATATATAATA   1560
ATAAAGTATG  TCTAATTAGG  TAGTTTTTCT  TTTTGAAAAC  TGAAATGAGA  AAAAGCAAAA   1620
CATAAAATTG  ACTTGAATGA  CAGCTACATG  ACATTTCAT   CTTGTAGTAG  GGACATATGA   1680
TTTGTTTTTT  TCCTTTGCCA  CATGTGTTCT  GTTATCCTTA  ATCTCCAAGT  AATCCCATAT   1740
TTTGGTTGAT  GATTCACAAT  ATAATCTATC  TAATTATGCA  CCTCCTTCTA  CTTAAAGAAG   1800
AAAAATGTGA  TGGCGATTGG  CAATTGGGAA  GATAATTAAA  ATCTGTTGAG  TACTCTTTCA   1860
TCCGCAATGG  CATTCAGTCG  ATGGAACAAT  AGTGAAAGAG  ATGTTTAAAA  AAATTATTTA   1920
CATTTAAAAT  GATTTTAGAT  TTGACGCAAT  CCGAAAAAAT  TAGTCTATAA  AAAAAATTAT   1980
TTAAAATCAT  GCAAGAGCTC  AATTAACTTC  ATCCGCCTTT  GATGTGAGTT  TTTCTACATT   2040
CATCACGCTT  CCCATCCCCG  AACCCCAACA  CTCTATACTC  CGATCCATGA  CGTGAACAAA   2100
TTATTCAAGC  GTTCAATTTG  ACTCTAATAT  CATACTAAAT  AAACCTAATT  TAATAGTAAA   2160
AATTAGCTTA  ACAATTTACT  AATTTCACAC  AATTTTTTAT  ATTGTTGTCT  TGTCATTATC   2220
TTTAGGTAAT  AATAGTGTAA  AAATTATCTT  ACACGATTAT  ACTACATAAT  TTATACGATT   2280
CGTTGATAAA  TTGTATACCA  AAGTGCCACC  TCATCACACA  ATAATTTAAT  TTGGACTAAG   2340
TTCACTATTA  GTGAATGAAT  GAATTTTAAT  TATAAATAGA  GGACTTGACA  AGATCATATT   2400
TGTATCAAAC  ACCATACACT  TTCTAAATTA  TCGATAGATT  TATTGTTTCA  GATG         2454
```

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (oligo)

( x i ) SEQUENCE DESCRIPTION: SEQ ID NO:4:

```
TGTTTCCCAT  GGAGGAGGAG                                                     20
```

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (oligo)

( x i ) SEQUENCE DESCRIPTION: SEQ ID NO:5:

```
CGAACTTGGT  GTTGCCCC                                                       18
```